United States Patent [19]
Watkins

[11] 4,088,602
[45] May 9, 1978

[54] DEHYDROGENATION CATALYST

[75] Inventor: Windell C. Watkins, Longview, Tex.

[73] Assignee: Eastman Kodak Company, Rochester, N.Y.

[21] Appl. No.: 776,016

[22] Filed: Mar. 9, 1977

Related U.S. Application Data

[60] Division of Ser. No. 583,936, Jun. 5, 1975, Pat. No. 4,029,695, which is a continuation-in-part of Ser. No. 498,885, Aug. 20, 1974, Pat. No. 3,975,301, which is a division of Ser. No. 409,823, Oct. 26, 1973, Pat. No. 3,855,279.

[51] Int. Cl.² ............................................. B01J 27/14
[52] U.S. Cl. ................................................... 252/437
[58] Field of Search ........................................ 252/437

[56] References Cited

U.S. PATENT DOCUMENTS

| | | | |
|---|---|---|---|
| 3,634,494 | 1/1972 | Tsu | 252/437 X |
| 3,828,101 | 8/1974 | Miklas | 252/437 X |

FOREIGN PATENT DOCUMENTS

| | | | |
|---|---|---|---|
| 818,584 | 7/1969 | Canada | 252/437 |
| 804,635 | 1/1969 | Canada | 252/437 |

*Primary Examiner*—Patrick P. Garvin
*Assistant Examiner*—William G. Wright
*Attorney, Agent, or Firm*—Edward R. Weber; Daniel B. Reece, III

[57] ABSTRACT

Lower aliphatic acids, e.g., isobutyric acid and esters, e.g., methyl isobutyrate are dehydrogenated in the presence of oxygen and a sold heterogenous dehydrogenation catalyst at temperatures in the range of from about 250° C. to about 600° C. The catalyst is the calcined residue of a base catalyst described as the mixed phosphates of iron and lead and a modifier component selected from the group consisting of manganese, uranium, praseodymium, calcium, strontium and chromium wherein such modifier is present in the amount of from about 0.1 to about 10% based on the weight of said base catalyst.

5 Claims, No Drawings

DEHYDROGENATION CATALYST

This application is a division of application Ser. No. 583,936 filed June 5, 1975 now U.S. Pat. No. 4,029,695 which in turn is a C.I.P. of Application Ser. No. 498,885 filed Aug. 20, 1974 now U.S. Pat. No. 3,975,301 which in turn is a divisional of Application Ser. No. 409,823 filed Oct. 26, 1973 now U.S. Pat. No. 3,855,279.

The invention relates to the synthesis of unsaturated lower aliphatic acids and esters of such acids by catalytic oxidative dehydrogenation of the corresponding saturated acids and esters.

The catalytic dehydrogenation of the lower alkane acids and their esters has been described in prior art. One known process has been carried out using a metal oxide catalyst but with no molecular oxygen present during the dehydrogenation. In such a process the catalyst is rapidly deactivated and requires frequent regeneration. Such a process operates with relatively low conversion per pass which increases operating costs and size of required equipment. See data presented in *Industrial and Engineering Chemical Products, Research and Development*, Volume II, p. 287 (1963) and U.S. Pat. No. 2,945,057. In another known process, dehydrogenation of lower alkane acids and their esters has been carried out with a metal sulfide oxidizing agent, but again without the presence of molecular oxygen. In that process the metal sulfide acts as a mild oxidizer which is chemically reduced and requires frequent regeneration. See U.S. Pat. No. 3,370,087.

U.S. Pat. No. 3,634,494 describes a process wherein the catalyst consists of the calcined mixed phosphates of iron, bismuth, and, in some embodiments, lead. The catalyst of U.S. Pat. No. 3,634,494 gives attractive conversions and yields; however, it suffers from a relatively short catalyst life. In addition, the catalyst cannot be satisfactorily regenerated to its original active state. Therefore, the process of U.S. Pat. No. 3,634,494 loses much of its attractiveness.

More recently U.S. Pat. No. 3,855,279 which issued from Application Ser. No. 409,823 which was the parent of Application Ser. No. 498,885 of which this application is a continuation-in-part described a two-component catalyst consisting of the calcined residue of the mixed phosphates of iron and lead.

Of the many catalytic systems described in the literature, including those detailed above, none have all the desirable properties of good catalysts. Among the criteria by which a catalyst is judged acceptable are high conversion and yield, long catalyst life and ease of regeneration to the original activity.

Accordingly, one of the objects of the instant invention is to provide an improved catalyst giving good conversions and yields and having a long catalyst life.

Another object of the instant invention is to provide a catalyst which can be easily regenerated to its original activity.

Yet another object of the invention is to provide a catalyst which can be simply prepared from readily available, inexpensive materials.

Yet another object of the invention is to provide a catalyst which provides an improvement over the catalysts described in the aforementioned U.S. Pat. No. 3,855,279.

These and other objects and advantages of the instant invention will become quite clear from the following description and the appended claims.

In accordance with the instant invention, a lower aliphatic acid or an ester thereof having the formula

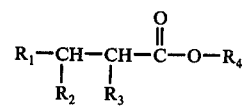

wherein $R_1$, $R_2$, $R_3$ and $R_4$ are selected from the group consisting of hydrogen and lower alkyl groups containing 1-4 carbon atoms, is selectively dehydrogenated to the $\alpha,\beta$-unsaturated equivalent acid or ester by contacting a gas-feed mixture comprising oxygen and the organic compound with an oxydehydrogenation catalyst which is described as a base catalyst comprising iron and lead combined with phosphorus and oxygen and a modifier component selected from the group consisting of manganese, uranium, praseodymium, calcium, strontium, and chromium wherein the modifier component is present in the amounts of from about 0.1% to about 10% based on the weight of the base catalyst. The catalyst can be described nominally as the residue resulting from calcining the phosphates of iron and lead in admixture with the modifier component. Dehydrogenation occurs at temperatures of from about 250° C to about 600° C., preferably from about 350° C. to about 500° C. For economy, a preferred pressure for the oxydehydrogenation is about atmospheric pressure, but the process may be carried out at pressures in the range of from about 0.3 atmosphere to about 10 atmospheres or higher if desired. Water, present as steam during the reaction, is found to improve the results of the process. The ratio of oxygen to saturated acid or ester in the feed mixture is preferably about 0.1 to about 6 gram atoms of oxygen per mole of compound to be dehydrogenated. If desired, the oxgen may be diluted with an inert gas such as helium, nitrogen, argon, etc. A preferred source of oxygen is air.

The catalysts of the instant invention consist of a base catalyst prepared as described in patent Ser. No. 3,855,279 to which has been added a metal modifier component selected from the group consisting of manganese, uranium, praseodymium, calcium, strontium, and chromium. In preparation of the improved catalyst of the instant invention the mixture of iron and lead phosphate described in the aforementioned U.S. Pat. No. 3,855,279 is precipitated by any of the procedures described in the said patent. Th precipitated base catalyst is then washed with an aqueous solution of a salt of one of the metals selected from the listed group and then dried. The dried catalyst is broken into particles of the desired size and calcined at a temperature of from about 400° C. to about 600° C. in accordance with the teachings of the aforementioned U.S. Pat. No. 3,855,279. Optionally, the catalyst may be pressed into tablets prior to calcining to get a more convenient catalyst shape. Other methods of depositing the metal ion modifier on the ferric phosphate-lead phosphate catalyst may be used, and the catalytic activity of the catalyst prepared by these methods would not be affected. The catalyst may be used in its calcined solid form without support, or it may be used on a catalyst support such as silica, silica-alumina, or silicon-carbide.

The process in which the subject catalyst is used involves the passage of a mixture of the feed-saturated acid or ester, water and air over the catalyst contained in a fixed bed. The temperature of the catalyst bed is maintained at from about 250° C. to about 600° C., a preferred range being from about 350° C. to about 500° C., and a more preferred range being from about 400° C. to about 450° C.

In practice, higher conversions and yields are obtained when several catalyst zones are used with mixing zones separating them. The total volume of air is added in portions above each catalyst zone. Most of the work with the catalyst of the invention has been carried out in a reactor with two catalyst zones and two air inlet points. The data obtained in a two-stage reactor can be related to a multistage reactor as has been demonstrated in U.S. Pat. No. 3,855,279.

The reactor effluent is cooled to condense a mixture composed mainly of water, unreacted feed acid or ester and product α,β-unsaturated acid or ester. The presence of water in the reactor facilitates the oxidative dehydrogenation reaction but its role in the reaction mechanism is unknown. Optimum concentration of water usually will be in the range of 0.5 to about 20 moles water per mole of feed acid or ester. However, up to about 40 moles of water per mole of acid or ester may be used.

The addition of a modifying metal can have one of two effects on the catalyst. First, the catalytic activity can be increased as shown by an increase in acid consumption; this is called promotion. Secondly, the catalyst can be poisoned as exemplified by a decrease in acid consumption. Neither of these descriptions of the effect the metal ion on the catalyst describes the selectivity of the resultant catalyst. The most desired catalyst would contain a metal which promotes activity and increases selectivity. However, a simple increase in selectivity can also be advantageous. The catalyst of U.S. Pat. No. 3,855,279 has been shown to be a very good catalyst for the oxidative dehydrogenation of isobutyric acid to methacrylic acid. The catalyst gives conversions of 50 ± 5% and selectivity of 75 to 95%. The catalysts of this invention can increase conversion by up to about 5% and selectivity up to about 8%. Such increases can be highly significant. For example, in a highly competitive commodities market such as exists in relation to methacrylic acid nominal improvements of 1 or 2% can make the difference between commercial acceptance and rejection of a process.

Previous work on the catalyst disclosed in U.S. Pat. No. 3,855,279 would lead one to believe that additional compounds present in the catalyst composition were detrimental to catalyst activity. It was shown that the presence of bismuth phosphate, bismuth oxide, silica, alumina, aluminum phosphate, and silicon carbide all promoted burning and carbon formation. It is therefore quite unexpected that trace amounts of certain metals in the catalyst composition could increase conversion and selectivity to a significant extent. The novelty of the discovery in the instant invention is further emphasized in the experimental section where it is demonstrated that only certain metals have a desirable effect upon the catalyst. The metal ion of the metal modifier may be present in amounts of from about 0.1% to about 10%, preferably from about 0.1% to about 3%. As will be appreciated the effective amount will vary depending on such factors as the metal modifier selected, the compound being dehydrogenated, the temperature of reaction, etc.

The invention is further illustrated by the following examples which are set forth for purposes of illustration only and should not be construed as limiting the invention in any manner.

EXAMPLES

The reactor used in these examples is a 1-inch by 30-inch Vycor tube with a thermowell in the center extending the length of the tube. At the top of the reactor are provisions for feeding air, isobutyric acid, and water. Another air inlet is positioned 10 inches from the bottom of the tube. Isobutyric acid and water are metered into the reactor through a calibrated pump. The rate of isobutyric acid addition is 40 milliliters per hour and water is fed at such a rate as to obtain the desired water to isobutyric acid mole ratio. Air is introduced into the reactor at two feed points through rotameters at such rates as to obtain the desired oxygen to isobutyric acid mole ratio. Sixty-nine percent of the air is fed to the top of the reactor and 31 percent is fed to the center. Two 20 milliliter catalyst beds are positioned in the reactor such that the central air inlet is between them. The volume between the catalyst beds and above the upper bed is filled with Vycor chips. The reactor is placed in an electric furnace and the temperature of the reactor is measured and controlled by means of thermocouples in the thermowell which are connected to temperature controllers.

The reactor effluent is condensed and collected. Every 24 hours the effluent is weighed and an aliquot analyzed by gas-liquid chromatography using an internal standard. The conversion, yield (selectivity), and percent isobutyric acid comsumption (activity) are calculated by the following equations.

$$\% \text{ conversion} = \frac{\text{moles MAA in product}}{\text{moles i-HOBu fed}} \times 100$$

$$\% \text{ yield (selectivity)} = \frac{\text{moles MAA in product}}{\text{moles i-HOBu fed - moles i-HOBu in product}} \times 100$$

$$\% \text{ i-HOBu consumption (activity)} = \frac{\text{moles i-HOBu fed - moles i-HOBu in product}}{\text{moles i-HOBu fed}} \times 100$$

$$= \frac{\% \text{ conversion}}{\% \text{ yield}} \times 100$$

where MAA = methacrylic acid
iHOBu = isobutyric acid

Also calculated for each run are water to isobutyric acid mole ratio, oxygen to isobutyric acid mole ratio, and contact time. Contact time ($\theta$) is defined by the following equation.

$$\theta = \frac{V_c \cdot 273}{V_g \cdot (273 + T)}$$

-continued where $V_c$ = volume of catalyst in milliliters
$V_g$ = total gas flow rate at STP in milliliters per second
$T$ = reactor temperature in ° C.

EXAMPLE 1

This example shows the variety of effects obtained by the presence of small amounts of various metal ions on the activity of the ferric phosphate-lead phosphate catalyst.

To a solution of 323 grams ferric nitrate enneahydrate and 160 grams lead nitrate in 1500 milliliters water is added 1500 milliliters of an aqueous solution containing 344 grams dibasic ammonium phosphate. The precipitate is removed by vacuum filtration, washed with 1500 milliliters of 2 weight percent aqueous metal salt, and dried at 120° C. for 24 hours. The catalyst cake is broken into 4–10 mesh particles and calcined at 550° C. for 2 hours. Catalysts prepared by this procedure are placed in the reactor and the following results obtained.

| | H$_2$O/i-HOBu | = 12.5 | |
| | O$_2$/i-HOBu | = 0.7 | |
| | $\theta$ | = 0.32 seconds | |

| Metal | Salt Used | Conversion (%) | Yield (%) | Activity (%) |
|---|---|---|---|---|
| None | — | 51 | 66 | 77 |
| K | Hydroxide | 37 | 47 | 78 |
| Mg | Acetate | 48 | 63 | 76 |
| Ca | Acetate | 53 | 67 | 79 |
| Sr | Acetate | 40 | 69 | 58 |
| Cr | Acetate | 53 | 68 | 78 |
| Mo | Phosphate | 11 | 22 | 50 |
| W | Acid | 15 | 55 | 27 |
| Mn | Acetate | 52 | 74 | 70 |
| Co | Nitrate | 43 | 63 | 68 |
| Ni | Chloride | 44 | 64 | 68 |
| Cu | Acetate | 37 | 55 | 67 |
| Zn | Chloride | 18 | 57 | 32 |
| Cd | Nitrate | 45 | 60 | 75 |
| Sn | Chloride | 45 | 62 | 73 |
| Bi | Nitrate | 38 | 64 | 60 |
| Pr | Nitrate | 56 | 70 | 80 |
| U | Acetate | 55 | 68 | 81 |
| Co | Nitrate | 47 | 64 | 73 |

As can be seen from the results above, the modifying metal ions which give the best overall results are manganese, praseodymium, and uranium. Of these, manganese gives the highest yield and lowest activity.

EXAMPLE 2

This example shows that the salt used for adding the modifying metal ion has little effect as long as the metal ion concentration in the wash solution is at the same level.

A catalyst is prepared by the procedure given in Example 1 except that a 1.5 percent manganous nitrate solution is used instead of the 2.0 percent manganese acetate solution. A comparison of the results obtained with these two catalysts is shown below.

| Temperature = 450° C. | $\theta$ = 0.3 second | |
| --- | --- | --- |
| H$_2$O/i-HOBu = 13 | O$_2$/i-HOBu = 0.7 | |
| | Acetate | Nitrate |
| % Conversion | 52 | 53 |
| % Yield | 74 | 74 |
| % Activity | 70 | 72 |

As can be seen, the results obtained are within experimental error in synthesis of catalyst and analysis of reactor effluent.

EXAMPLE 3

This example shows that the modifying metal ion must be present in the catalyst at low concentrations in order to obtain the desired modification to the catalyst.

A catalyst is prepared according to the procedure using manganese acetate in the wash solution. The concentration of the salt is varied from 1 percent to 3 percent. The results obtained from these catalysts are shown below.

| Temperature = 450° C. | | $\theta$ = 0.3 second | |
| --- | --- | --- | --- |
| H$_2$O/i-HOBu = 12 | | O$_2$/i-HOBu = 0.7 | |
| [Mn(OAc)$_2$] in Wash (%) | Conversion (%) | Yield (%) | Activity (%) |
| 1 | 51 | 70 | 73 |
| 1.5 | 55 | 73 | 74 |
| 2 | 52 | 74 | 70 |
| 3 | 28 | 63 | 44 |

The results indicate a greatly diminished activity is obtained when the manganese concentration is greater than 2 percent in the wash solution.

EXAMPLE 4

This example shows the wide range of temperatures over which a modified catalyst may be used and still be effective.

A catalyst modified by washing with 2 percent aqueous manganese acetate is used in the reactor of Example 1. The reactor temperatures are varied from 376° C. to 475° C. The following results are obtained.

| H$_2$O/i-HOBu = | 12 | | |
| --- | --- | --- | --- |
| O$_2$/i-HOBu = | 0.7 | | |
| $\theta$ = | variable with temperature only | | |
| Temperature (° C.) | Conversion (%) | Yield (%) | Activity (%) |
| 375 | 34 | 74 | 46 |
| 400 | 46 | 76 | 61 |
| 425 | 51 | 77 | 66 |
| 450 | 53 | 76 | 70 |
| 475 | 54 | 73 | 74 |

Although maximum yield is obtained at 425° C. there is only a small drop in yield at ±25° C. Thus, a reactor containing this catalyst is not so sensitive to temperature as to make its operation difficult.

Although the invention has been described in considerable detail with reference to certain preferred embodiments thereof, it will be understood that variations and modification can be affected without departing from the spirit and scope of the invention as described hereinabove and in the appended claims.

I claim:

1. A catalyst consisting of the calcined residue of a mixture of (a) a base component consisting essentially of the phosphates of iron and lead wherein the atomic ratio of the metals is defined by 1 Fe/$x$ Pb where $x$ is from about 0.1 to about 10, and (b) a modifier component selected from the group consisting of manganese, uranium, praseodymium, calcium, strontium and chromium wherein said modifier component is present in amounts of from about 0.1% to about 10% based on the weight of the base component.

2. A catalyst according to claim 1 wherein $x$ has a value of from about 0.5 to about 1.5.

3. A catalyst according to claim 1 wherein the modifier component is present in the amount of from about 0.1% to about 3% based on the weight of the base component.

4. A catalyst according to claim 1 prepared by the steps of
   (1) preparing a solution of salts of iron and lead,
   (2) precipitating from said solution a mixture of ferric phosphate and lead phosphate,
   (3) adding a modifier component selected from the group consisting of manganese, uranium, praseodymium, calcium, strontium and chromium wherein said modifier will be present in an amount of from about 0.1 to about 10% based on the weight of the mixture of ferric phosphate and lead phosphate,
   (4) drying the modified precipitate,
   (5) adjusting the size and shape of the catalyst particles to that desired for process use, and
   (6) calcining said adjusted particles at a temperature of from about 400° C. to about 600° C.

5. A process according to claim 4 wherein the modifier component is added by washing the precipitate of ferric phosphate and lead phosphate with an aqueous solution of a salt of the selected modifying metal.

* * * * *